(12) United States Patent (10) Patent No.: US 9,085,779 B2
Kratochvil et al. (45) Date of Patent: Jul. 21, 2015

(54) PROCESSES FOR PRODUCING $H_2S$ USING SULPHUR-REDUCING BACTERIA

(75) Inventors: David Kratochvil, Vancouver (CA); Maxmillian Nodwell, Vancouver (CA); Michael Bratty, Vancouver (CA)

(73) Assignee: BIOTEQ ENVIRONMENTAL TECHNOLOGIES INC., Vancouver (CA)

( * ) Notice: Subject to any disclaimer, the term of this patent is extended or adjusted under 35 U.S.C. 154(b) by 451 days.

(21) Appl. No.: 12/867,482

(22) PCT Filed: Feb. 12, 2009

(86) PCT No.: PCT/CA2009/000179
§ 371 (c)(1),
(2), (4) Date: Jan. 14, 2011

(87) PCT Pub. No.: WO2009/100537
PCT Pub. Date: Aug. 20, 2009

(65) Prior Publication Data
US 2011/0104776 A1 May 5, 2011

Related U.S. Application Data

(60) Provisional application No. 61/064,039, filed on Feb. 12, 2008.

(51) Int. Cl.
*C12P 3/00* (2006.01)
*C12M 1/107* (2006.01)
(Continued)

(52) U.S. Cl.
CPC ........ *C12P 3/00* (2013.01); *C12M 21/04* (2013.01); *C12M 23/36* (2013.01); *C12M 29/24* (2013.01); *C12M 41/26* (2013.01); *Y02E 50/343* (2013.01)

(58) Field of Classification Search
USPC ............... 435/168; 423/564, 234.08, 244.07; 280/99, 213, 226
See application file for complete search history.

(56) References Cited

U.S. PATENT DOCUMENTS 2,722,480 A 11/1955 Tuhin Kumar et al.
2,789,033 A 4/1957 Huggins et al.
(Continued)

FOREIGN PATENT DOCUMENTS

WO WO 98/58737 12/1998
WO WO 2010/017652 2/2010

OTHER PUBLICATIONS

Huisman et al. Biologically produced sulphide for purification of process streams and effluent treatment and recovery of metals in the metal and mining industry. Hydrometallurgy 2006. vol. 83, pp. 106-113.*

(Continued)

*Primary Examiner* — Jon P Weber
*Assistant Examiner* — Kara Johnson
(74) *Attorney, Agent, or Firm* — Knobbe, Martens, Olson & Bear, LLP

(57) ABSTRACT

There is provided a process for producing $H_2S$ comprising: a) continuously providing an electron donor at a variable rate to a biosolution comprising sulphur-reducing bacteria; b) reacting elemental sulphur with $HS^-$ to from soluble polysulphide; c) providing said polysulphide to a bioreactor having the biosolution, thereby producing $H_2S$ gas in the bioreactor; and d) continuously removing $H_2S$ gas from the bioreactor, wherein an average rate of providing polysulphide to sulphur-reducing bacteria is equal to an average rate of polysulphide consumption by the sulphur-reducing bacteria.

63 Claims, 3 Drawing Sheets

(51) Int. Cl.
*C12M 1/00* (2006.01)
*C12M 1/34* (2006.01)

(56) References Cited

U.S. PATENT DOCUMENTS

| | | | | |
|---|---|---|---|---|
| 3,327,898 | A | * | 6/1967 | Farr .................................. 222/1 |
| 3,714,444 | A | * | 1/1973 | Carr et al. ...................... 250/574 |
| 3,896,660 | A | * | 7/1975 | Valentyik ..................... 73/61.67 |
| 4,110,400 | A | | 8/1978 | Jha et al. |
| 4,332,774 | A | * | 6/1982 | Drum et al. ................... 422/111 |
| 4,547,347 | A | | 10/1985 | Lussiez et al. |
| 4,917,874 | A | | 4/1990 | Sheth et al. |
| 5,269,936 | A | | 12/1993 | Gussmann et al. |
| 6,059,974 | A | | 5/2000 | Scheurman, III |
| 6,150,133 | A | * | 11/2000 | Mead et al. ................... 435/69.1 |
| 6,203,700 | B1 | * | 3/2001 | Rose et al. .................... 210/602 |
| 6,387,669 | B1 | * | 5/2002 | Truex et al. ................... 435/168 |
| 6,852,305 | B2 | * | 2/2005 | Buisman et al. .............. 423/564 |
| 2003/0192832 | A1 | | 10/2003 | Bowers |

OTHER PUBLICATIONS

Everett, D.J. et al., The treatment of underground mine waters for the removal of calcium and sulphates by a GYP-CIX process, International Mine Water Association & Zambia Consolidated Copper Mines Limited: The First African Symposium on Mine Drainage and Environment Protection from Mine Waste Water Disposal, 1993, pp. 463-491.

Huisman, J. et al., Biologically produced sulphide for purification of process streams, effluent treatment and recovery of metals in the metal and mining industry, Hydrometallurgy, 2006, vol. 83, pp. 106-113.

International Search Report issued on May 21, 2009, for International Application No. PCT/CA2009/000179.

Robinson et al., The treatment of acid effluent from the Grootvlei Mine using novel IX techniques, Journal—South African Institute of Mining and Metallurgy, 1998, vol. 98, Issue 7, pp. 343-352.

BioteQ Environmental Technologies Inc., Annual Report, 2001, 30 pages.

Buisman, Cees J.N., Sulphur and sulphate reduction with acetate and propionate in an aerobic process for sulphide removal, Applied Microbiology and Biotechnology, 1989, vol. 32, pp. 363-370.

Caiqiao, Yin et al., Treatment of solution from atmospheric sulfuric acid leaching of ocean polymetallic nodules, Beijing General Research Institute of Mining and Metallurgy, Beijing, China.

International Network for Acid Prevention: Treatment of sulphate in mine effluents, Lorax Environmental, Oct. 2003, pp. 129 pages.

Office Action dated Nov. 12, 2010, issued in connection with Australian Application No. 2007234313.

Robinson, R.E. et al., The treatment of acid effluent from the Grootvlei Mine using novel IX techniques, 1998.

Robinson, R.E., The Amanzi concept for acid mine drainage, Science in Africa, May 2003.

Schoeman, J.J. et al., Investigation into alternative water treatment technologies for the treatment of underground mine water discharged by Grootvlei Proprietary Mines Ltd into the Blesbokspruit in South Africa, Desalination, 2001, vol. 133, pp. 13-30.

Wurts, William A. et al., Interactions of pH, carbon dioxide, alkalinity and hardness in fish ponds, Southern Regional Aquaculture Center Publication, Dec. 1992, Issue 464.

* cited by examiner

PROCESSES FOR PRODUCING H₂S USING SULPHUR-REDUCING BACTERIA This application is U.S. National Phase of International Application PCT/CA2009/000179, filed Feb. 12, 2009 designating the U.S., and published in English as WO 2009/100537 on Aug. 20, 2009, which claims priority to U.S. Provisional Application No. 61/064039 filed Feb. 12, 2008.

TECHNICAL FIELD

This invention relates to the field of bioreactors, in particular processes for producing $H_2S$ from elemental sulphur using sulphur-reducing bacteria.

BACKGROUND

Biological $H_2S$ production is a complex process and the rate of this process may be subject to many disturbances including chemical feed quality, sulphur particle size, pH, conductivity, and temperature. At the same time, the capacity of an $H_2S$ supply system to respond rapidly to changes and fluctuations in the $H_2S$ demand by the end user of the $H_2S$, for example, an industrial process, is important to a successful integration of the biological $H_2S$ generation process into industrial applications.

The traditional processes for the production of hydrogen sulphide from the bacterial reduction of a mixture of a liquid and elemental sulfur with an electron donor can be difficult to control and prone to swings in production rates. These control difficulties can make the processes unsuitable for commercial application, where a continuous, reliable source of $H_2S$ is desired. Biebl and Pfenning (1978) describe culture types and culture media for the reduction of elemental sulfur using acetate, among other compounds. Buisman (1989) describes optimal pH and temperature regimes for such cultures, as well as investigates substrate and product limitations. U.S. Pat. No. 6,852,305 describes a process for $H_2S$ production using elemental sulfur and an electron donor, such as hydrogen gas, carbon monoxide or organic compounds. The bacteria may be *Desulforomanas* sp (mesophilic), *Desulfotomaculum* KT7 (thermophilic), etc. The liquid/sulfur mixture is at a pH ranging from 5 to 9, and the liquid/sulfur mixture contacts the bacteria at a hydraulic retention time of at least 1 day. The hydrogen sulphide is stripped from the liquid medium to produce a gas containing at least 1 volume percent hydrogen sulphide. In Huisman (2006), the reaction of sulfide with elemental sulphur to form polysulphides, which are then used by bacteria as an electron acceptor, is described, along with early attempts to commercialize the $H_2S$ generator process for the treatment of acid rock drainage (ARD).

SUMMARY

This invention is based, in part, on systems and methods for providing suitable reactor conditions in order to be able to adapt a single bioreactor to provide a variety of required outputs, while providing a constant environment for the living components of the bioreactor, needed for the commercialization of the biological hydrogen sulphide generator. A constant concentration of substrates, reactants and/or conditions may be provided in the biosolution of the bioreactor for maintenance of the biosolution by providing variable administration of the substrates, reactants and/or conditions in the biosolution. This invention is also based, in part, on the recognition of problems associated with process integration of U.S. Pat. No. 6,852,305 with other industrial processes. In particular, industrial processes, often require $H_2S$ to be provided at a variable rate or at a particular rate with no or little variability being acceptable.

Industrial processes that consume sulfide may impose strict criteria on the sulfide supplied from bioreactors as follows: a) the rate of $H_2S$ supply must be constant with little or no room for the $H_2S$ production in the bioreactor to deviate from the set demand rate; or b) the rate of $H_2S$ supply must be variable matching the sulfide demand of the sulfide consuming process that is subject to sulfide demand fluctuations (both predictable and unpredictable) on timescales ranging from minutes to hours or days. Both of a) and b) may be encountered in the field of wastewater treatment, mineral processing, and metal extraction where $H_2S$ is used.

Bioreactors and the living components thereof can be very sensitive to their environment and particular conditions. If appropriate conditions, for example relatively steady state conditions or other suitable conditions, are not provided to or maintained in biosolutions in bioreactors then the bioreactors may not work very efficiently or may stop functioning altogether. For example, if products are not withdrawn at a suitable rate from a bioreactor, this can upset the appropriate conditions for the bioreactor. Furthermore, if substrates and/or reactants are not provided to the bioreactor at a suitable rate, this can also upset the appropriate conditions for the bioreactor. Examples of conditions that affect bioreactors operation include the chemical composition of the biosolution, the rate of supply of substrates for the microbial population residing in the bioreactor, and the rate of removal of the product of microbial activity from the bioreactor.

In illustrative embodiments of the present invention, there is provided a process for producing $H_2S$ gas from a culture of sulphur-reducing bacteria in a biosolution in a bioreactor, the process comprising: feeding elemental sulphur and an electron donor to the culture at a selected sulfur-to-electron donor ratio; maintaining the concentration of bisulphide and polysulphide species dissolved in the biosolution at a concentration that supports a desired rate of elemental sulfur dissolution, so that polysulphide is provided to the culture at an average rate that is equal to an average rate of polysulphide consumption by the culture; and, removing $H_2S$ gas from the bioreactor.

In other illustrative embodiments of the present invention, there is provided a process for producing $H_2S$ comprising: a) continuously providing an electron donor at a variable rate to a biosolution comprising sulphur-reducing bacteria; b) reacting elemental sulphur with $HS^-$ to from soluble polysulphide; c) providing said polysulphide to a bioreactor having the biosolution, thereby producing $H_2S$ gas in the bioreactor; and d) continuously removing $H_2S$ gas from the bioreactor, wherein an average rate of providing polysulphide to the sulphur-reducing bacteria is equal to an average rate of polysulphide consumption by the sulphur-reducing bacteria.

In other illustrative embodiments of the present invention, there is provided a process for producing $H_2S$ gas from a culture of sulphur-reducing bacteria in a biosolution in a bioreactor, the process comprising: feeding elemental sulfur and an electron donor to the culture at a selected sulfur-to-electron donor ratio; reacting elemental sulfur with HS" to form water soluble polysulphides, maintaining a sufficient inventory of suspended solid sulfur and dissolved polysulphides in the bioreactor to support the desired rate of $H_2S$ production, and removing $H_2S$ gas from the bioreactor, wherein an average rate of providing polysulphide to sulphur-reducing bacteria is equal to an average rate of polysulphide consumption by the sulphur-reducing bacteria.

In other illustrative embodiments of the present invention, there is provided a process for producing $H_2S$ comprising: a) continuously providing an electron donor at a variable rate to a biosolution comprising sulphur-reducing bacteria; b) maintaining the respective concentrations of any one or more of: bisulphide, polysulphide, electron donor and/or bicarbonate species dissolved in the biosolution at levels that support a desired rate of elemental sulfur dissolution, so that polysulphide formed during the sulfur dissolution process is provided to the microbial culture at an average rate that is equal to the average rate of polysulphide consumption by the culture, and c) continuously removing $H_2S$ gas from the bioreactor, wherein the rate of removing $H_2S$ from the bioreactor is equal to the rate of $H_2S$ production.

In other illustrative embodiments of the present invention, there is provided a process for producing $H_2S$ comprising: a) continuously providing an electron donor at a variable rate to a biosolution comprising sulphur-reducing bacteria; b) reacting elemental sulphur with $HS^-$ to form soluble polysulphide; c) maintaining said polysulphide inventory in the bioreactor at a level necessary to yield the required rate of $H_2S$ production; d) maintaining constant concentrations of bisulphide, and bicarbonate in the bioreactor to support the required rate of $H_2S$ production; and e) continuously removing $H_2S$ gas from the bioreactor, wherein an average rate of providing polysulphide to sulphur-reducing bacteria is equal to an average rate of polysulphide consumption by the sulphur-reducing bacteria.

In other illustrative embodiments of the present invention, there is provided a process described herein wherein the $H_2S$ gas is removed by stripping with an inert gas. In other illustrative embodiments of the present invention, there is provided a process described herein wherein the $H_2S$ gas is removed by stripping with at least one of the following gases: nitrogen, carbon dioxide, carbon monoxide, methane, and/or hydrogen, or a mixture containing the inert gas and at least one of the following gases: nitrogen, carbon dioxide, carbon monoxide, methane, and/or hydrogen. The inert gas may be nitrogen. The inert gas and/or gas mixture used for $H_2S$ stripping may be recycled in part or in full. The flowrate of gas that is allowed to exit the bioreactor may be adjusted to maintain the pH in the bioreactor at pH>about pH 6.8 and often at pH>about pH 7.5. The $H_2S$ gas may be removed continuously or periodically.

In other illustrative embodiments of the present invention, there is provided a process described herein wherein the removing $H_2S$ gas from the bioreactor comprises providing $H_2S$ gas to a contactor.

In other illustrative embodiments of the present invention, there is provided a process described herein wherein the gas exiting the contactor is returned to the bioreactor in part or in full.

In other illustrative embodiments of the present invention, there is provided a process described herein wherein the removing $H_2S$ gas from the bioreactor comprises passing $H_2S$ gas through a sulphur trap. The sulphur trap may remove foam and/or elemental sulfur and solution droplets entrained in the gas stream.

In other illustrative embodiments of the present invention, there is provided a process described herein wherein the removing $H_2S$ gas from the bioreactor comprises providing $H_2S$ gas to an alkali sulphide trap, thereby producing a sulphide laden solution. The pH in the alkali sulphide trap may be controlled by adding alkali to the alkali sulphide trap. The alkali may be in liquid or solid form. The alkali may be selected from the group consisting of: lime, lime slurry, sodium hydroxide, sodium carbonate, and mixtures thereof. A change in a level of material in the alkali-sulphide-trap may be used to determine the variable rate of providing the electron donor to the biosolution.

In other illustrative embodiments of the present invention, there is provided a process described herein further comprising directing the sulphide laden solution to a contactor.

In other illustrative embodiments of the present invention, there is provided a process described herein wherein the elemental sulphur is reacted as particles ranging in size from about 20 microns to about 400 microns, and often as particles ranging in size from about 20 microns to about 200 microns. The elemental sulphur may be reacted as particles ranging in size from about 50 microns to about 150 microns. The elemental sulphur may be reacted as a slurry comprising sulphur and at least one of the group consisting of: water, lime, soda ash solution, sodium hydroxide solution, biosolution, and alkali sulphide. The slurry may comprise from about 20% to about 60% w/w solids. The slurry may comprise from about 30% to about 60% w/w solids.

In other illustrative embodiments of the present invention, there is provided a process of removing of the excess liquid and/or slurry from the bioreactor via a sulphur trap. Solid sulfur removed from the liquid and/or slurry in the trap may be recycled in part or in full to the bioreactor. A change in an amount of settled volume of sulphur in the biosolution may be used to determine the variable rate of providing the electron donor and/or sulphur to the biosolution.

In other illustrative embodiments of the present invention, there is provided a process of maintaining sufficient concentration of suspended elemental sulphur in the bioreactor based on a periodic measurement of suspended solids in the bioreactor at least once a day using either "settled sulfur technique" or any one of the common analytical techniques for analyzing slurries or determining total suspended solids.

In other illustrative embodiments of the present invention, there is provided a process described herein wherein the technique for determining the concentration of solid sulfur is as follows: a) a well mixed sample of the bioreactor slurry containing biosolution and solid sulphur particles suspended in biosolution is poured into a graduated container such as a graduation cylinder; b) fixed amount of time is allowed for solids contained in the sample to settle to the bottom of the container; c) volume of the settled solids is recorded.

In other illustrative embodiments of the present invention, there is provided a process described herein wherein the biosolution is maintained such that a substantially constant concentration of electron donor, bisulphide, bicarbonate, and/or polysulphide is provided in the biosolution. The maintenance may comprise: a) obtaining a sample of the biosolution, b) titrating the sample with a mineral acid and recording the volumes of mineral acid required to reduce a pH of the biosolution from its original pH to pH "M" and pH "L"; where M represents a pH value in the range of from about pH 4 to about pH 7 and often in the range of from about pH 5.3 to about pH 5.6 and L represents a pH value in the range of from about pH 2 to about pH 5 and often in the range of from about pH 3 to about pH 3.6, c) repeating steps a) and b) at least once; d) adjusting the variable rate of providing the electron donor to the biosolution based on the recorded volumes of mineral acid required to reduce the pH of the biosolution from pH M to pH L. An increasing trend in the titrating recorded volume of mineral acid consumed between pH M and pH L may be indicative of a need to decrease the variable rate of providing the electron donor to the biosolution and a decreasing trend in titrating recorded volume may be indicative of the potential to achieve a sustainable increase in the rate of $H_2S$ production by increasing the variable rate of providing the electron donor to the biosolution without any negative impact on bioreactor operation in the short and/or long terms. Any mineral acid can be used but often HCl is used. The concentration of acid may range from about 0.001N to about 1 N and is often is from about 0.01 to about 0.5 N. The biosolution sample volume may range from about 10 mL to about 2 L and often is from about 25 mL to about 500 mL. When the concentration of HCl is about 0.12N HCl, and a volume of the sample may be about 250 ml, the volume of HCl required to reduce the pH of the sample from pH M to pH L being greater than about 25 mL is indicative of a need to decrease the variable rate of providing the electron donor to the biosolution. Methods may further comprise e) adjusting the addition of any of the following: carbonate, bicarbonate, or hydroxide of alkali earth or alkali metals including Na, K, Ca, Mg to the bioreactor so that the volume of the mineral acid required to reduce the biosolution sample pH from its original pH to pH L is constant with each successive titration. The decreasing trend in the volume of acid required to reduce the biosolution sample pH from its original pH to pH L with each successive titration indicates that the addition of the alkali earth or alkali metals should be increased. The increasing trend in the volume of acid required to reduce the biosolution sample pH from its original pH to pH L with each successive titration indicates that the addition of the alkali earth or alkali metals should be decreased.

In other illustrative embodiments of the present invention, there is provided a process described herein wherein biosolution is maintained such that a substantially constant concentration of bisulphide, sodium bisulphide, bicarbonate and/or polysulphide is provided in the biosolution. The maintenance may comprise: a) obtaining a sample of the biosolution, b) titrating the sample with a mineral acid and recording the volumes of mineral acid required to reduce a pH of the biosolution to about pH 5.5 and about pH 3.5; c) repeating steps a) and b) at least once; and d) adjusting the variable rate of providing the electron donor to the biosolution based on the recorded volumes of mineral acid required to reduce the pH of the biosolution to about pH 5.5 and about pH 3.5. An increasing trend in titrating recorded volume may be indicative of a need to decrease the variable rate of providing the electron donor to the biosolution and a decreasing trend in titrating recorded volume may be indicative of a need to increase the variable rate of providing the electron donor to the biosolution. The mineral acid may be about 0.12N HCl, and a volume of the sample may be about 250 ml. A volume of HCl required to reduce the pH of the sample from about pH 5.5 to about pH 3.5 being greater than about 25 mL is indicative of a need to decrease the variable rate of providing the electron donor to the biosolution. A volume of HCl required to reduce the pH of the sample from about pH 5.5 to about pH 3.5 being less than about 25 mL is indicative of a need to increase the variable rate of providing the electron donor to the biosolution.

In other illustrative embodiments of the present invention, there is provided a process described herein whereby an increasing trend in the settled sulphur volume recorded would be used to: a) decrease the rate of electron donor addition to the bioreactor when the volume of about 0.12N HCl required to drop the biosolution pH from pH M to pH L shows an increasing trend; b) adjust the rate of addition of water and/or sulfur to the grinding circuit to increase the circuit efficiency; and c) identify the point in time during the bioreactor ramp-up (for example, following start-up and/or re-start after plant shut-down) when the rate of electron addition to the bioreactor can be increased provided that the volume of about 0.12N HCl required to drop the biosolution pH from pH M to about pH L is below about 25 mL and not showing an increasing trend.

In other illustrative embodiments of the present invention, there is provided a process described herein wherein the pH of the biosolution is maintained at a pH greater than about pH 7.5 by controlling the flow of biogas that is allowed to exit the bioreactor;

In other illustrative embodiments of the present invention, there is provided a process described herein wherein the pH of the biosolution is maintained at a pH greater than about pH 7.5 by controlling the flow of biogas that is allowed to exit the bioreactor and/or flow of gas that is allowed to enter the bioreactor;

In other illustrative embodiments of the present invention, there is provided a process described herein wherein the pH of the biosolution is maintained at a pH greater than about pH 7.5. Maintenance of pH may be achieved by the combination of a) controlling the flow of biogas allowed to exit the bioreactor b) controlling the flow of gas that is allowed to enter the bioreactor; and c) addition of carbonate, bicarbonate, and/or hydroxide of alkali or alkali earth metals including Na, Ca, and Mg to the bioreactor.

In other illustrative embodiments of the present invention, there is provided a process of maintaining constant pressure in the bioreactor vessel at a setpoint that is greater than atmospheric pressure by the addition of inert gas to the bioreactor.

In other illustrative embodiments of the present invention, there is provided a process comprising immediate stoppage of hydrogen and/or carbon monoxide addition to the bioreactor when the pressure inside the bioreactor reaches the maximum design limit of the bioreactor vessel.

In other illustrative embodiments of the present invention, there is provided a process described herein wherein species of photoautotrophs, namely algae, are grown using light and a source of nutrients to sequester carbon from the atmosphere, these algae are treated, and this treated algae liquor is fed the $H_2S$ generating bioreactor as an electron donor, and as a carbon source.

In other illustrative embodiments of the present invention, there is provided a process described herein wherein the biosolution is maintained such that a substantially constant concentration of bisulphide, bicarbonate, and/or polysulphide is provided in the biosolution. The maintenance may comprise: a) obtaining a sample of the biosolution, b) applying a resting period to allow solids to settle, c) titrating an aliquot volume of a stock solution containing Cu and dilute mineral acid with biosolution (free of sulfur) until the ORP (Oxidation-Reduction-Potential) of the stock solution aliquot is reduced from the original ORP value before the titration to ORP L, d) recording the volume of biosolution consumed during the titration, e) repeating steps a) and d) at least once; e) adjusting the variable rate of providing hydrogen and/or carbon monoxide to the biosolution based on the recorded volumes of biosolution required to reduce the ORP of the copper laden stock solution from the original ORP to ORP L. A decreasing trend in the titrating recorded volume of biosolution consumed may be indicative of a need to decrease the variable rate of providing hydrogen and/or carbon monoxide to the biosolution and an increasing trend in titrating recorded volume may be indicative of the potential to achieve a sustainable increase in the rate of $H_2S$ production by increasing the variable rate of providing hydrogen and/or carbon monoxide to the biosolution without any negative impact on bioreactor operation in the short and/or long terms. The redox titration is performed using the following:

Copper concentration in the stock solution may range from 0.01 to 10 g/L and is often about 6 g/L;

The concentration of mineral acid in the stock solution may range from 0.02 to 0.5N and is often about 0.2 N;

The aliquot volume of the stock solution used during the titration may range from 10 to 1000 mL and is often about 100 mL;

The ORP value L may range from −150 mV to +250 mV and often ranges from about −50 mV to about +150 mV; and The ORP values are all expressed using Ag/AgCl reference.

In other illustrative embodiments of the present invention, there is provided a process described herein wherein the biosolution is maintained such that a substantially constant concentration of bisulphide, bicarbonate, and/or polysulphide is provided in the biosolution. The maintenance may comprise applying the acid-base titration in conjunction with the redox titration as per the descriptions presented above.

In other illustrative embodiments of the present invention, there is provided a process described herein wherein the conductivity of the biosolution is maintained at between about 6 mS/cm and about 25 mS/cm. Maintenance of conductivity may be achieved by the addition of carbonate, bicarbonate, or hydroxide of alkali or alkali earth metals including Na, Ca, and Mg to the bioreactor.

In other illustrative embodiments of the present invention, there is provided a process described herein wherein the total volume of mineral acid consumed to bring the pH of the biosolution sample from the value recorded before the titration to about pH L is used together with or instead of the conductivity measurement.

In other illustrative embodiments of the present invention, there is provided a process described herein wherein a rate of $H_2S$ gas production by said sulphur-reducing bacteria is maintained at a maximum rate.

DETAILED DESCRIPTION

Figure 1:
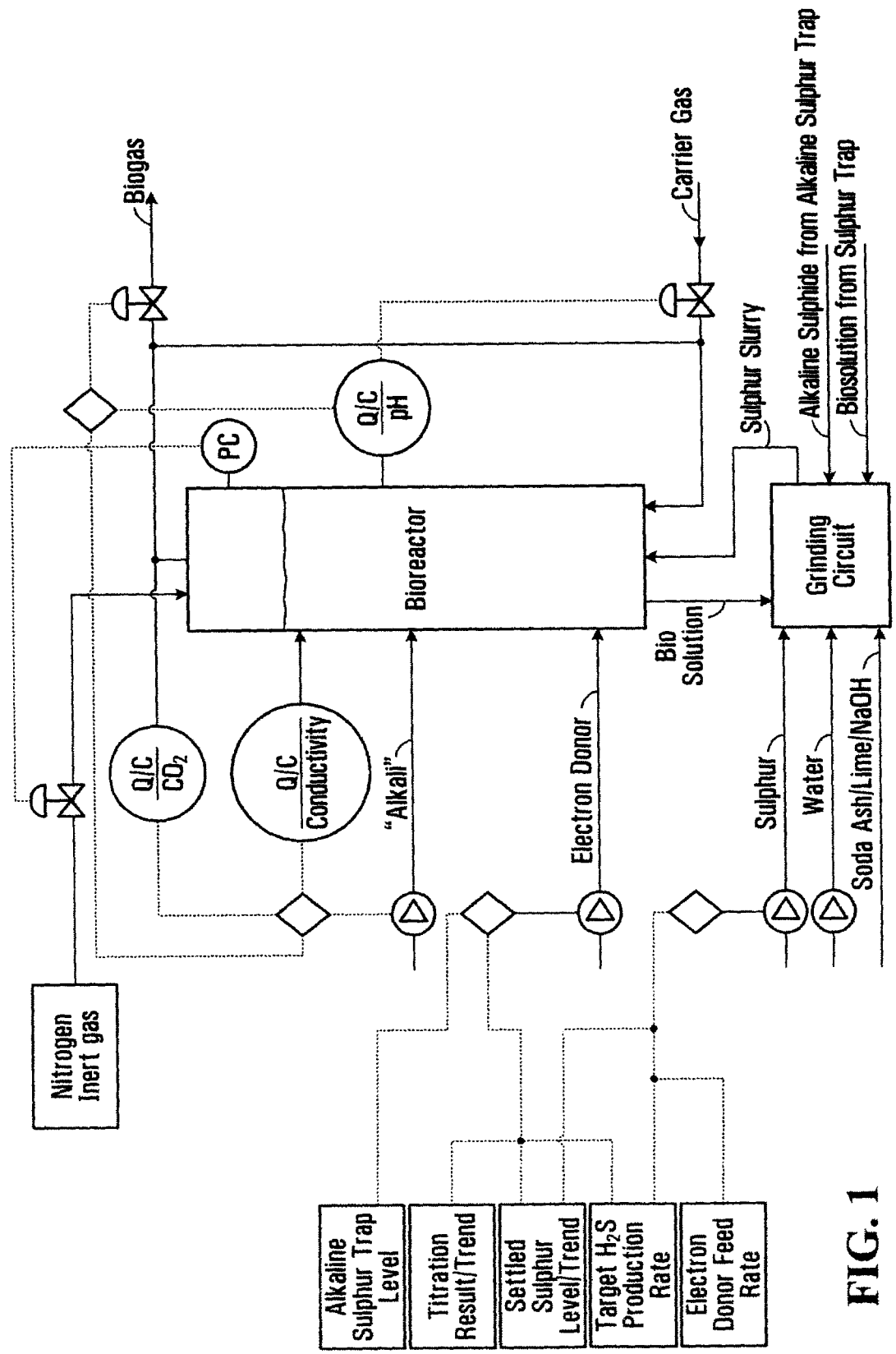
FIG. 1 is a process flow diagram illustrating one embodiment of a methodology of control of processes described herein to provide a high rate of polysulphide formation by controlling a) biosolution chemistry, and b) elemental sulphur feed and inventory in the bioreactor. Various process control and quality control points are identified by 'PC circles' and/or 'Q/C circles'.

In illustrative embodiments, there is provided a process for producing $H_2S$ comprising: a) continuously providing an electron donor at a variable rate to a biosolution comprising sulphur-reducing bacteria; b) reacting elemental sulphur with $HS^-$ to from soluble polysulphide; c) providing said polysulphide to a bioreactor having the biosolution, thereby producing $H_2S$ gas in the bioreactor; and d) continuously removing $H_2S$ gas from the bioreactor, wherein an average rate of providing polysulphide to sulphur-reducing bacteria is equal to an average rate of polysulphide consumption by the sulphur-reducing bacteria.

An electron donor is a compound or composition that oxidizes easily. The electron donor provides an electron to the reaction, wherein the molecule of electron donor comprises at least one less electron after the reaction is complete. Examples of electron donors include, but are not limited to: hydrogen, carbon monoxide, alcohols, fatty acids and mineral salts of fatty acids, other readily degradable organic compounds and mixtures thereof. Examples of alcohols include, but are not limited to, primary alcohols, secondary alcohols, methanol, ethanol, n-propanol, n-butanol, etc and mixtures thereof. Examples of fatty acids and their salts include, but are not limited to acetic acid/acetate, propionic acid/propionate, butyric acid/butyrate, adipic acid/adipate, maleic acid/maleate, oleyl lactylic acid, linoleyl lactylic acid, linolenoyl lactylic acid, stearoyl lactylic acid, palmitoyl lactylic acid, myristoyl lactylic acid, lauroyl lactylic acid, caproyl lactylic acid, etc and lactates and mixtures thereof. Mixtures of electron donors are also suitable for use in particular embodiments of the present invention. When hydrogen is used as an electron donor it is often advantageous to include in the biosolution a carbon source for the sulphur-reducing bacteria. In many circumstances where hydrogen is used as an electron donor, it is advantageous to provide a carbon source that may be metabolized by the sulphur-reducing bacteria such that $CO_2$ is produced. Alternatively or additively, $CO_2$ can be added to the biosolution in addition to hydrogen being provided as an electron donor.

Methane may be produced from the electron donor in the bioreactor if methanogenic bacteria are present. In some cases it may be advantageous to add methane to the gas mixture used for stripping $H_2S$ from the biosolution as it may assist in inhibiting methane production and promote electron donor uptake by the sulphur-reducing bacteria. The control of the sulphide content on the reactor is also used to control the growth of methanogenic bacteria.

A biosolution is a composition that is provided in the bioreactor in which sulphur-reducing bacteria can live, grow and metabolize elemental sulphur to form reduced sulphur and $H_2S$. The biosolution is often everything that is contained within the bioreactor that is not the sulphur-reducing bacteria. Since the sulphur-reducing bacteria consume or metabolize some of the constituents of the biosolution, a biosolution may be a dynamic composition. Many biosolutions are known in the art and biosolutions are often specifically tailored to meet the needs of particular bacteria and/or the desired result of the bioreactor. Biosolutions are often described by their dynamic properties as opposed to their composition.

Sulphur-reducing bacteria are bacteria that are capable of reducing sulphur and generating $H_2S$. Examples of sulphur-reducing bacteria include, but are not limited to: species of the genera *Desulfovibrio*, *Desulfotomaculum* (*Desulfotomaculum KT7* (thermophilic)), *Desulfomonas* (*Desuforomonas* sp. (mesophilic)), *Desulfobulbus*, *Desulfobacter*, *Desulfococcus*, *Desulfonema*, *Desulfosarcina*, *Desulfobacterium*, *Desulforomas*, *Methonococcus* and *Methanobacterium*. Examples of specific sulphur-reducing bacteria species include, but are not limited to: *Desulforolobus ambivalnes*, *Acidianus infernus*, *Acidianus brierley*, *Stygiolobus azoricus* (mesophilic), *Thermoproteus neutrophilus*, *Thermoproteus tenax*, *Thermodiscus maritimus* (thermophilic), *Pyrobaculum islandicum*, *Pyrodictium occultum*, and *Pyrodictium brockii* (hyperthermophilic), or mixtures thereof.

Polysulphide is a group of chemical entities encompassed by the formula $HS_x^-$, where x is greater than one. Typically these chemical entities are soluble and x may range from 2 to 6, often x is from 3 to 5. Polysulphide consumption by sulphur-reducing bacteria is the process by which sulphur-reducing bacteria metabolize and convert polysulphide into other chemical entities, such as $H_2S$. Polysulphide consumption by sulphur-reducing bacteria has a rate which is a variable rate depending in part on the composition of the biosolution and the conditions in the bioreactor.

A bioreactor is a receptacle, container or vessel used for bioprocessing. In other words, a contained vessel or other structure in which chemical reactions are carried out and mediated by a biological system, enzymes or cells. In the case of the present invention, the biological system mediating the chemical reactions are sulphur-reducing bacteria although other bacteria such are methanogenic bacteria may also be present. Bioreactors provide one or more inlets for providing some or all of the substrates required for the biological system to grow, live and metabolize as desired and one or more outlets for removing some or all of the waste and non-waste products of the chemical reactions that occur in the bioreactor. In particular embodiments of the present invention, operating bioreactors may receive sulphur slurry, electron donor solution, soda ash solution, and aqueous solutions of various macro and micro-nutrients. The gaseous products of sulphur-reducing bacteria in a bioreactor are often referred to as biogas. The biogas may be removed from the bioreactor using a carrier gas. Bioreactors often have a fixed volume, though the volume may be large, small or in between. Bioreactors, whether fixed volume or not, may provide an outlet for bleeding biosolution. The bleeding outlet may provide additional control of the composition of the contents of the bioreactor and its output. The solution that is withdrawn in this manner is called "the bleed".

The microbial activity of sulphur-reducing bacteria may be negatively affected by the presence of oxygen and air ingress into the bioreactor should be prevented. In other illustrative embodiments of the present invention, there is provided a process described herein wherein air ingress into the bioreactor is prevented by maintaining a positive pressure (greater than atmospheric) in the bioreactor using inert gas such as nitrogen.

In other illustrative embodiments of the present invention, there is provided a process described herein wherein removing $H_2S$ gas from the bioreactor includes passing $H_2S$ gas through a sulphur trap. A sulphur trap is a receptacle, container or vessel that may be used to separate unreacted sulphur from the biosolution that is bled from the bioreactor and/or other outputs from the bioreactor. Separation of the unreacted sulphur may be achieved by settling or by centrifugation. The sulphur trap may reduce sulphur reagent loss and may increase the bioreactor's efficiency with respect to sulphur consumption. Furthermore, the sulphur trap may prevent sulphur from being introduced into downstream processes such as those in a contactor.

In other illustrative embodiments of the present invention, there is provided a process described herein wherein removing $H_2S$ gas from the bioreactor comprises providing $H_2S$ gas to an alkali sulphide trap (AST), thereby producing a sulphide laden solution. In particular illustrative embodiments of the present invention, a change in a level of material in the alkali-sulphide-trap may be used to determine the variable rate of providing the electron donor to the biosolution. The alkali sulphide trap is discussed in more detail below. The pH in the alkali sulphide trap may be controlled by adding alkali to the alkali sulphide trap. The alkali may be in liquid form or in solid form and may be, but not limited to lime, lime slurry, sodium hydroxide, sodium carbonate and mixtures thereof. The sulphide laden solution may be directed to a contactor.

A contactor is a device in which the $H_2S$ is contacted with a process stream to transfer the $H_2S$ to the process stream. The type of contactor and the process stream may vary depending on the end use for the $H_2S$. For example, the contactor may be a continuously stirred tank reactor (CSTR), spray tower, bubble column or an autoclave in which a metal containing process stream is contacted with the $H_2S$. The type of contactor is mainly dependent on fluid (liquid and/or gas) flow rate, the $H_2S$ concentration and the concentration of the active species (e.g. metal) in process stream. In particular illustrative embodiments, the contactor may be a device to facilitate concentration of the $H_2S$ by contacting the $H_2S$ with a process stream that absorbs $H_2S$ and transports it to a regeneration column to concentrate the $H_2S$ for use in a variety of different industrial processes. The contactor may be a membrane in which the $H_2S$ is selectively removed and concentrated. Other contactors are known to a person of skill in art and may be used in processes described herein.

Processes described herein may be operated at temperatures of from about 15° C. to about 90° C. Typically the processes are carried out at temperatures from about 25° C. to about 75° C. Often a temperature is selected depending on the type of sulphur-reducing bacteria in the bioreactor and the suitable temperature conditions for those particular bacteria. Such temperature conditions are known to a person of skill in the art.

Processes described herein may be operated at pH's of from about pH 5 to about pH 9. Typically the processes are carried out at a pH above about pH 7.5. The particular pH may be selected depending on the type of sulphur-reducing bacteria in the bioreactor and the suitable pH conditions for those particular bacteria. Such pH conditions are known to a person of skill in the art.

The process conditions that maximize the rate of sulphur dissolution may be achieved through a process control strategy that combines process automation with maintenance of desired bioreactor conditions by adjusting the input and output of the bioreactor based on activity measurements. Low cost sulphur, such as the by-products from the oil and gas industry, may be used for biological $H_2S$ production with high efficiency of sulphur utilization. Undesirable fluctuations and sudden disruptions in the biogenic $H_2S$ production may be reduced, minimized and/or eliminated and $H_2S$ production rate and bioreactor activity may be maximized at all times.

The rate of biological $H_2S$ production from chemical elemental sulphur may be maximized through process controls that yield conditions in the bioreactor that maximize the rate of sulphur dissolution and the efficiency of sulphur utilization. The process controls may include, but are not limited to:
  a) Continuous electron donor addition based on target $H_2S$ production rate, biosolution titration measurement, settled sulphur test, and/or level in Alkali Sulphide Trap (AST);
  b) Bioreactor pH control by controlling the flow of biogas that is allowed to exit the bioreactor system, $CO_2$ measurement in the biogas, and/or flow of carrier gas allowed to enter the bioreactor system;
  c) Bioreactor pH control by the addition of soluble alkali to the bioreactor; and/or
  d) Biosolution ionic strength control by the addition of alkali or alkali earth bicarbonate, carbonate, or hydroxide based on the biosolution titration measurement.

The efficiency of sulphur utilization may be increased by incorporating:
  a) Wet grinding of chemical elemental sulphur to a specific particle size distribution;

b) Addition of lime, soda ash solution, biosolution, and/or alkali sulphide produced in the AST to the grinding process;

c) Adjustments to a sulphur grinding circuit based on the "settled sulphur test"; and d) incorporating a Sulphur Trap vessel in the plant design.

Integration of biogenic $H_2S$ production into industrial processes with fluctuating $H_2S$ demand may be achieved by adding an AST and associated process controls. Furthermore, production of calcium based sulphide reagents in the AST by dissolving lime in the presence of $H_2S$ can be coupled with biogenic $H_2S$ production for the purpose of producing reagent grade $Ca(HS)_2$.

Biological $H_2S$ production from elemental sulphur may be a two-step process. The two steps are consecutive rather than in parallel. In the first step, elemental sulphur reacts with $HS^-$ (bisulphide) ions to form soluble polysulphide species such as $HS_3^-$, $HS_4^-$, and $HS_5^-$. In the second step, elemental sulphur contained in the polysulphides is converted into the S(-II) form by the sulphur-reducing bacteria.

The formation of polysulphide species, often referred to as the process of sulphur dissolution, is a chemical reaction that does not require the involvement of bacteria. The main reactants involved include bisulphide ions and sulphur. Polysulphide species act as a catalyst of sulphur dissolution thus making polysulphide formation an autocatalytic process.

The sulphur-reducing bacteria convert sulphur contained in polysulphides into $H_2S$ gas that may be continuously removed from the bioreactor via stripping with a carrier gas, which is often an inert gas, such as nitrogen or a mixture containing the inert gas and at least one of the following gases: nitrogen, carbon dioxide, carbon monoxide, and/or hydrogen. The inert gas and/or gas mixture used for $H_2S$ stripping may be recycled in part or in full. The flowrate of gas that is allowed to exit the bioreactor may be adjusted to maintain the pH in the bioreactor at pH>about pH 6.8 and often at pH>about pH 7.5. The $H_2S$ gas may be removed continuously or periodically. The carrier gas may be recycled.

The pre-requisite conditions for successful continuous production of $H_2S$ is that at all times the average rate of polysulphide formation must be equal to the average rate of polysulphide consumption, (i.e. the biological conversion of polysulphide sulphur into $H_2S$ gas). If polysulphide consumption is faster than sulphur dissolution, then the concentration of both polysulphide and bisulphide ions in the biosolution decreases causing a decrease in the rate of sulphur dissolution and ultimately in the rate of $H_2S$ gas formation. If the polysulphide inventory is completely depleted, the sulphur-reducing bacteria will have no more substrate to convert and the $H_2S$ production in the bioreactor will cease completely.

In particular illustrative embodiments of processes described herein a constant high rate of polysulphide formation may be maintained by controlling a) the biosolution chemistry, and b) the elemental sulphur feed and inventory in the bioreactor. An illustrative methodology of the control is depicted in FIG. 1 and described in more detail below.

The biosolution chemistry control depicted in FIG. 1 is able to maintain a constant concentration of bisulphide, polysulphide, bicarbonate, and electron donor species in solution so that a high rate of sulphur dissolution rate is maintained. The control is achieved through the combination of the following:

a) Control of biosolution pH at a pH greater than about pH 7.5 by adjustments in the flow of biogas that is allowed to exit the bioreactor system and/or carrier gas allowed to enter the bioreactor system;

b) Control of biosolution pH at a pH greater than about pH 7.5 and biosolution conductivity between about 6 mS/cm and about 25 mS/cm by the addition of hydroxide, carbonate, or bicarbonate of alkali metals or alkali earth metals and/or mixtures thereof. The conductivity set-point is site specific and depends on the $CO_2$ concentration in biogas. The $CO_2$ concentration in biogas varies with the type of electron donor and the type of $H_2S$ gas consuming process that is being supplied with $H_2S$ from the bioreactor. The higher the $CO_2$ concentration the higher the conductivity setpoint;

c) Continuous (variable rate) addition of electron donor;

d) Adjustment to the variable rate of electron donor addition based on the results of biosolution titration, the target production rate of $H_2S$, settled sulphur test, and/or the level in the AST;

e) adjusting the rate of addition of alkali to the bioreactor based on the results of biosolution titration;

f) Ratio of sulphur-to-electron donor fed into the bioreactor controlled based on the target rate of $H_2S$ production;

g) Control of biosolution temperature.

The biosolution titration is a technique for assessing the composition of biosolution primarily with respect to the electron donor inventory in the bioreactor and bisulphide concentration in the biosolution. A sample of the biosolution is titrated using a strong mineral acid such as HCl. The biosolution sample of at least about 25 mL, often at least about 50 mL and often at least about 250 mL is poured into a beaker or other suitable container and placed on a magnetic stirrer (or other suitable stirring device), often inside a fumehood. A pH probe is inserted into the sample and vigorous mixing is applied. Mineral acid solution is introduced into the bisolution sample under the vigorous mixing conditions.

The volumes of mineral acid required to reduce a pH of the biosolution from its original pH to pH "M" and pH "L"; where M represents a pH value in the range of from about pH 4 to about pH 7 and often in the range of from about pH 5.3 to about pH 5.6 and L represents a pH value in the range of from about pH 2 to about pH 5 and often in the range of from about pH 3 to about pH 3.6, is recorded. In illustrative embodiments, the volume of acid required to bring the biosolution pH down to about pH 5.5, and about pH 3.5 is recorded. An increasing trend in the recorded titrating volumes of mineral acid consumed between pH M and pH L may be indicative of a need to decrease the variable rate of providing the electron donor to the biosolution and a decreasing trend in titrating recorded volume may be indicative of the potential to achieve a sustainable increase in the rate of $H_2S$ production by increasing the variable rate of providing the electron donor to the biosolution without any negative impact on bioreactor operation in the short and/or long terms. For example, if the consumption of about 0.12N HCl required to drop the biosolution pH from pH M to pH L in about 250 mL sample is greater than about 25 mL and/or the trend of the last three titrations is increasing, such as 8, 12, 20 mL, then the rate of electron donor addition could be decreased. If a higher rate of $H_2S$ production is required in response to an increased demand for $H_2S$ in the downstream process and if the consumption of about 0.12N HCl required to drop the biosolution pH from pH M to pH L in about 250 mL sample is lower than about 25 mL then the rate of electron donor addition can be increased to meet the higher demand. Control may also be provided by adjusting the addition of any of the following: carbonate, bicarbonate, or hydroxide of alkali earth or alkali metals including Na, K, Ca, Mg to the bioreactor so that the volume of the mineral acid required to reduce the biosolution sample pH from its original pH to pH L is constant with each successive titration. The decreasing trend in the volume of acid required to reduce the biosolution sample pH from its original pH to pH L with each successive titration indicates that the addition of the alkali earth or alkali metals should be increased. The increasing trend in the volume of acid required to reduce the biosolution sample pH from its original pH to pH L with each successive titration indicates that the addition of the alkali earth or alkali metals should be decreased.

Ionic species of different alkali metals and alkali earth metals possess different conductivities in aqueous solutions. Therefore, the titration may replace or be used in conjunction with the conductivity measurement to control the addition of alkali to the bioreactor.

When gaseous electron donors such are hydrogen and carbon monoxide are used in the process of $H_2S$ production in the bioreactor, a "redox" titration may be used instead or in conjunction with the "acid-base" titration technique described above for adjusting the electron donor addition to the bioreactor as follows. In other illustrative embodiments of the present invention, there is provided a process described herein wherein the biosolution is maintained such that a substantially constant concentration of bisulphide, bicarbonate, and/or polysulphide is provided in the biosolution. The maintenance may comprise: a) obtaining a sample of the biosolution, b) applying a resting period to allow solids to settle, c) titrating an aliquot volume of a stock solution containing Cu and dilute mineral acid with biosolution (free of sulfur) until the ORP (Oxidation-Reduction-Potential) of the stock solution aliquot is reduced from the original ORP value before the titration to ORP L, d) recording the volume of biosolution consumed during the titration, e) repeating steps a) and d) at least once; e) adjusting the variable rate of providing hydrogen and/or carbon monoxide to the biosolution based on the recorded volumes of biosolution required to reduce the ORP of the copper laden stock solution from the original ORP to ORP L. A decreasing trend in the titrating recorded volume of biosolution consumed may be indicative of a need to decrease the variable rate of providing hydrogen and/or carbon monoxide to the biosolution and an increasing trend in titrating recorded volume may be indicative of the potential to achieve a sustainable increase in the rate of $H_2S$ production by increasing the variable rate of providing hydrogen and/or carbon monoxide to the biosolution without any negative impact on bioreactor operation in the short and/or long terms. The redox titration is performed using the following:

Copper concentration in the stock solution may range from 0.01 to 10 g/L and is often about 6 g/L;

The concentration of mineral acid in the stock solution may range from 0.02 to 0.5N and is often about 0.2 N;

The aliquot volume of the stock solution used during the titration may range from 10 to 1000 mL and is often about 100 mL;

The ORP value L may range from −150 mV to +250 mV and often ranges from about −50 mV to about +150 mV;

The ORP values are all expressed using Ag/AgCl reference.

When gaseous electron donors such are hydrogen and carbon monoxide are used in the process of $H_2S$ production in the bioreactor, the concentration of electron donor species in solution is not detectable by the acid-base titration. The purpose of the redox titration is to establish the inventory of bisulphide and polysulphide.

Chemical elemental sulphur may be supplied in the form of pills or granules varying in size from about 1.3 mm to about 3.5 mm. In order to increase the rate of $H_2S$ production by maximizing the rate of sulphur dissolution, particle size of sulphur must be reduced and the fresh surfaces of sulphur created during grinding must be conditioned. FIG. 1 depicts that the particle size reduction in illustrative embodiments of processes described herein may be achieved via wet grinding whereby sulphur, water, soda ash solution, and/or alkali sulphide are either premixed and then fed into a grinding circuit or fed directly into the grinding circuit. The resultant sulphur slurry may contain from about 20% to about 60% w/w solids, and often more than about 30% w/w solids. Various types of conventional grinding equipment can be used including ball mills, rod mills, vertimill, or vibratory mill. Sulphur particles size smaller than about 200 micron and often smaller than about 150 micron in the feed to the bioreactor may achieve a high rate of sulphur dissolution and high efficiency of sulphur utilization. Very fine sulphur particles, i.e. smaller than about 20 micron, but possibly as large as about 50 micron are likely to float and/or dissolve slower than larger particles. This is due to flotation of the particles and the lower shear in the liquid phase layer adjacent to the surface of the particle, compared to the larger particle. The lack of shear is due in part to the notion that small/fine particles move at almost the same speed as the liquid in agitated tanks such as the bioreactor. Shear is helpful for fast mass transfer of bisulphide and polysulphide diffusing between the surface of sulphur particles and the bulk of the biosolution. Particle size distribution produced by grinding in the grinding circuit can be controlled by conventional classifiers, hydrocyclones, and vibratory screens.

Figure 2:
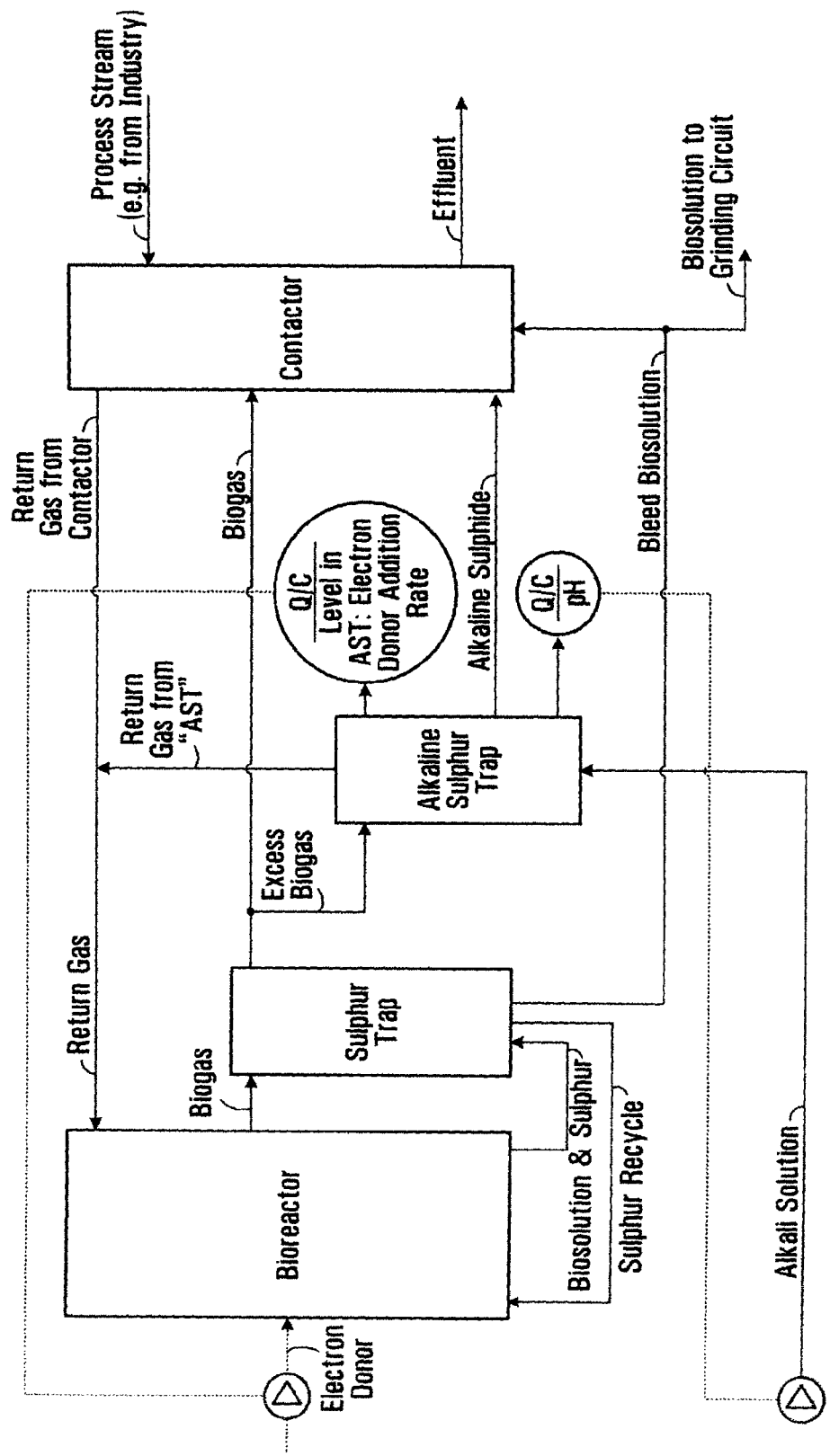
FIG. 2 is a process flow diagram illustrating one embodiment of integration of a sulphur-trap (ST) into processes described herein. Various process control and quality control points are identified by 'Q/C circles'.

An operating bioreactor may receive sulphur slurry, electron donor solution, soda ash solution (for adjustment of conductivity), and aqueous solutions of various macro and micro-nutrients. This results in the level in the bioreactor increasing and a certain amount of biosolution may be withdrawn from the bioreactor in order to compensate for the addition of these materials. The solution that is withdrawn from the bioreactor is called "the bleed". A Sulphur Trap may be included in the process design and is shown in FIG. 2. The sulphur trap may provide:

a) separation of unreacted solid sulphur from bioreactor bleed solution by settling. The use of the sulphur trap may reduce sulphur reagent loss and hence increases sulphur utilization. The removal of solid sulphur from the bleed also prevents sulphur from being introduced into downstream processes, such as in the contactor tank; and b) removal of foam carried over from biogas from the bioreactor. Foaming may occur in the bioreactor from time to time. Foam often contains fine elemental sulphur. Removal of foam from biogas helps to capture sulphur particles and return them to the biological process. Furthermore, the sulphur trap may prevent foam from migrating downstream where it could damage process equipment such as compressors and be undesirable from the point of view of the downstream process quality control.

Depending on the efficiency of sulphur grinding and resultant particle size distribution, the concentration of solid sulphur in the bioreactor may vary from about 5 g/L to about 50 g/L. The volume of solids that settle to the bottom of the bisolution sample placed in a graduated cylinder may be used to represent the concentration of sulphur in the biosolution as a whole. Depending on the average sulphur particle size and the $H_2S$ production rate, the volume of settled sulphur typically varies from about 80 mL to about 350 mL per 1000 mL of biosolution. Under normal operation and at a constant rate of $H_2S$ production, the settled volume should remain constant. Changes in the settled sulphur measurement may be used in the overall process control as follows:

a) when the rate of $H_2S$ production is constant, an increase in the settled sulphur measurement may indicate a decrease in the grinding circuit efficiency. Adjustments of water and sulphur additions to the grinding circuit may be made in order to increase the grinding efficiency and reduce the average sulphur particle size;

b) during a ramp-up of $H_2S$ production, when the volume of about 0.12N HCl required to drop the biosolution pH from about pH 5.5 to about pH 3.5 is lower than about 25 mL in a sample of about 250 mL biosolution and does not show an increasing trend, the rate of electron donor addition to the biosolution may be held constant (and not increased) until the settled sulphur measurement shows an increasing trend at which time the rate of electron donor addition to the biosolution is increased;

c) when the settled sulphur measurement shows an increasing trend and the volume of about 0.12N HCl required to drop the biosolution pH from about pH 5.5 to about pH 3.5 shows an increasing trend, then the rate of electron donor addition to the bioreactor may be decreased.

Biological $H_2S$ production is a complex process and the rate of this process may be subject to many disturbances including chemical feed quality, sulphur particle size, pH, conductivity, and temperature. At the same time, the capacity of an $H_2S$ supply system to respond rapidly to changes and fluctuations in the $H_2S$ demand by the end user of the $H_2S$ (represented in FIG. 2 by the contactor, for example, an industrial process, is important to a successful integration of the biological $H_2S$ generation process into industrial applications. In order to allow the biological $H_2S$ production process to respond quickly to changes in the $H_2S$ demand by the end user, an Alkali Sulphide Trap (AST) may be incorporated into the process design as part of the interface between the bioreactor and the end user's process. When the rate of $H_2S$ production exceeds the rate of $H_2S$ consumption in the contactor, excess $H_2S$ may be directed into the AST. The pH in the AST may be controlled by adding liquid alkali such as lime slurry or solutions of sodium hydroxide or sodium carbonate to the AST. Thus the level in AST rises when the rate of production of $H_2S$ in the bioreactor exceeds the demand for $H_2S$. When the rate of $H_2S$ consumption/demand exceeds the rate of $H_2S$ production then sulphide laden solution stored in the AST may be directed to the contactor. The changes in the level in the AST reflect the balance between $H_2S$ supply and $H_2S$ demand. Therefore, the level in AST may be used in the control of the electron donor addition to the bioreactor.

Figure 3:
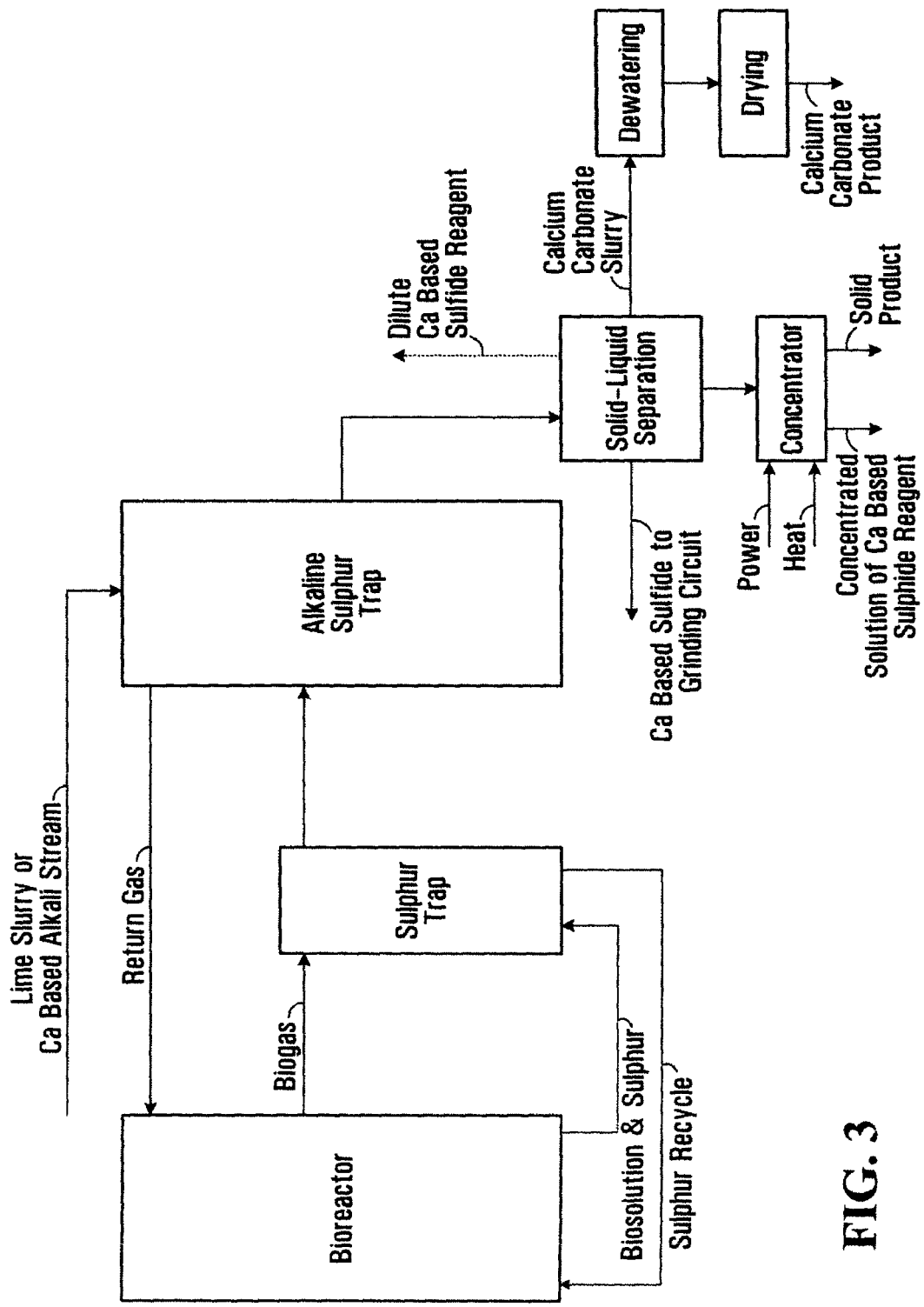
FIG. 3 is a process flow diagram illustrating one embodiment of integration of an alkaline-sulphur-trap (AST) into processes described herein.

The AST may also be used for manufacturing calcium (Ca) based sulphide reagents for commercial sale. Such a process is depicted in FIG. 3. Dissolving hydrated lime in the presence of $H_2S$ gas yields Ca based sulphide reagents. The composition and purity of the Ca-based reagents may vary depending on process conditions such as pH, magnesium content, biogas composition, and temperature. Either concentrated lime slurry, or the industrial process with pH adjusted with calcium based alkali, may be used as feed streams for making calcium based sulphide reagents in the AST. The calcium based reagents produced in the AST may substitute NaSH in industrial processes. This may provide lower cost of alkaline sulphide reagent; improved pH control in the end user's process; improved efficiency of the end user's process due to the reduction or elimination of sodium from the process; and precipitated calcium carbonate as a by-product available for sale or use in the industrial process.

The manufacturing process for Ca and Mg based sulphide reagents may include a solid-liquid separation step where calcium carbonate is produced, and a concentration step where heat and/or mechanical energy may be applied to produce either a concentrated solution or crystallized solid product of the calcium based sulphide reagents for sale Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. The word "comprising" is used herein as an open-ended term, substantially equivalent to the phrase "including, but not limited to" and the word "comprises" has a corresponding meaning. As used herein, the singular forms "A", "an" and "the" include plural referents unless the context clearly dictates otherwise. Thus, for example, reference to "a thing" includes more than one thing. Citation of references herein is not an admission that such references are prior art to the present invention. Any priority document(s) and all publications, including, but not limited to, patents and patent applications, cited in this specification are incorporated herein by reference as if each individual publication were specifically and individually indicated to be incorporated by reference herein and as though fully set forth herein. The invention includes all embodiments and variations substantially as herein before described and with reference to the examples and drawings.

What is claimed is:

1. A process for producing $H_2S$ gas from a culture of sulphur-reducing bacteria in a biosolution in a bioreactor, the process comprising:

feeding elemental sulphur and an electron donor to the culture at a selected sulfur-to-electron donor ratio;

maintaining biosolution chemistry so that the concentration of bisulphide and polysulphide species dissolved in the biosolution is at a substantially constant concentration that supports a selected rate of elemental sulfur dissolution, so that polysulphide is provided to the culture in the biosolution at an average rate that is equal to an average rate of polysulphide consumption by the culture in the biosolution; and, removing $H_2S$ gas from the bioreactor;

wherein the step of maintaining biosolution chemistry comprises:

adjusting the flow rate of $H_2S$ gas that is removed from the bioreactor to maintain the pH in the bioreactor at a pH greater than about pH 6.8, or greater than about 7.5; and maintaining the conductivity of the biosolution at between about 6 mS/cm and about 25 mS/cm by the addition of carbonate, bicarbonate, or hydroxide of alkali or alkali earth metals to the bioreactor.

2. The process of claim 1, wherein the $H_2S$ gas is removed by stripping with a gas.

3. The process of claim 2, wherein the gas is an inert gas.

4. The process of claim 3, wherein the inert gas is nitrogen.

5. The process of claim 2, wherein the gas is selected from the group consisting of nitrogen, carbon dioxide, carbon monoxide, methane, and/or hydrogen, or a mixture containing an inert gas and at least one of the following gases: nitrogen, carbon dioxide, carbon monoxide, methane, and/or hydrogen.

6. The process of claim 2, wherein the gas used for $H_2S$ stripping is recycled in part or in full.

7. The process of claim 1, wherein the $H_2S$ gas is removed continuously.

8. The process of claim 1, wherein the $H_2S$ gas is removed periodically.

9. The process of claim 1, wherein the step of removing $H_2S$ gas from the bioreactor is followed by providing the $H_2S$ gas to a contactor.

10. The process of claim 9, further comprising returning at least a portion of the gas exiting the contactor to the bioreactor.

11. The process of claim 1, wherein removing the $H_2S$ gas from the bioreactor is followed by passing the $H_2S$ gas through an off-gas sulphur trap.

12. The process of claim 11, wherein the off-gas sulphur trap removes foam and/or elemental sulfur and/or solution droplets entrained in the gas removed from the bioreactor.

13. The process of claim 1, wherein the step of removing $H_2S$ gas from the bioreactor is followed by providing the $H_2S$ gas to an alkali sulphide trap.

14. The process of claim 13, wherein a sulphide laden solution is produced in the alkali sulphide trap.

15. The process of claim 14, wherein a change in a level of material in the alkali sulphide trap is monitored, and is used to determine the variable rate of providing the electron donor to the biosolution.

16. The process of claim 14, further comprising directing the sulphide laden solution to a contactor.

17. The process of claim 13, wherein the pH in the alkali sulphide trap is controlled by adding an alkali to the alkali sulphide trap.

18. The process of claim 17, wherein the alkali is in liquid form.

19. The process of claim 17, wherein the alkali is in solid form.

20. The process of claim 17, wherein the alkali is selected from the group consisting of: lime, lime slurry, sodium hydroxide, sodium carbonate, and mixtures thereof.

21. The process of claim 1, wherein the elemental sulphur is reacted as particles ranging in size from about 20 microns to about 400 microns.

22. The process of claim 1, wherein the elemental sulphur is reacted as particles ranging in size from about 20 microns to about 200 microns.

23. The process of claim 1, wherein the elemental sulphur is reacted as particles ranging in size from about 50 microns to about 150 microns.

24. The process of claim 1, wherein the elemental sulphur is reacted as a slurry comprising sulphur and at least one further component selected from the group consisting of: water, lime, soda ash solution, sodium hydroxide solution, biosolution, and alkali sulphide.

25. The process of claim 24, wherein the slurry comprises from about 20% to about 60% w/w solids.

26. The process of claim 24, wherein the slurry comprises from about 30% to about 60% w/w solids.

27. The process of claim 24, wherein an excess of liquid and/or slurry is removed from the bioreactor via an excess-fluid sulphur trap.

28. The process of claim 27, wherein solid sulfur is removed from the excess liquid and/or slurry in the excess-fluid sulphur trap.

29. The process of claim 28, wherein the solid sulfur removed from the excess liquid and/or slurry is recycled in part or in full to the bioreactor.

30. The process of claim 1, wherein a change in an amount of settled volume of sulphur in the biosolution is monitored, and is used to determine the variable rate of providing the electron donor and/or sulphur to the biosolution.

31. The process of claim 1, further comprising maintaining a selected concentration of suspended elemental sulphur in the bioreactor based on a periodic measurement of suspended solids in the bioreactor.

32. The process of claim 31, wherein the measurement of suspended solids is at least once a day.

33. The process of claim 31, wherein the measurement of suspended solids is made using a settled sulfur technique.

34. The process of claim 33, wherein the settled sulfur technique comprises:
   a) delivering a sample of the bioreactor slurry containing biosolution and solid sulphur particles suspended in the biosolution into a graduated container;
   b) allowing solids contained in the sample to settle in the container;
   c) recording the volume of settled solids in the container.

35. The process of claim 31, wherein the measurement of suspended solids is made by determining total suspended solids.

36. The process of claim 31, wherein an increasing trend in the settled sulphur volume is followed by decreasing the rate of electron donor addition to the bioreactor.

37. The process of claim 1, wherein the biosolution is maintained such that a substantially constant concentration of electron donor and bicarbonate is provided in the biosolution.

38. The process of claim 37, wherein the maintenance of concentrations in the biosolution comprises:
   a) obtaining a sample of the biosolution,
   b) titrating the sample with a mineral acid and recording the volumes of mineral acid required to reduce a pH of the biosolution from its original pH to pH "M" and pH "L"; where M represents a pH value in the range of from about pH 4 to about pH 7, or in the range of from about pH 5.3 to about pH 5.6; and, L represents a pH value in the range of from about pH 2 to about pH 5, or in the range of from about pH 3 to about pH 3.6;
   c) repeating steps a) and b) at least once;
   d) adjusting the variable rate of providing the electron donor to the biosolution based on the recorded volumes of mineral acid required to reduce the pH of the biosolution from pH M to pH L.

39. The process of claim 38, wherein an increasing trend in the volume of mineral acid consumed between pH M and pH L is followed by the step of decreasing the variable rate of providing the electron donor to the biosolution.

40. The process of claim 38, wherein a decreasing trend in the volume of mineral acid consumed between pH M and pH L is followed by increasing the variable rate of providing the electron donor to the biosolution to achieve an increase in the rate of $H_2S$ production.

41. The process of claim 38, wherein the mineral acid is HCl.

42. The process of claim 41, wherein the concentration of HCl is about 0.12N HCl, and a volume of the sample is about 250 ml, and a measurement of the volume of HCl required to reduce the pH of the sample from pH M to pH L being greater than about 25 mL is followed by decreasing the variable rate of providing the electron donor to the biosolution.

43. The process of claim 38, wherein the mineral acid concentration range is from about 0.001 N to about 1 N.

44. The process of claim 38, wherein the mineral acid concentration range is from about 0.01 to about 0.5 N.

45. The process of claim 38, wherein the biosolution sample volume is from about 10 mL to about 2 L.

46. The process of claim 38, wherein the biosolution sample volume is from about 25 mL to about 500 mL.

47. The process of claim 38, further comprising:
   e) adjusting the addition of any one or more of the following: carbonate, bicarbonate, or hydroxide of an alkali earth or alkali metals including Na, K, Ca, Mg to the bioreactor, so that the volume of the mineral acid required to reduce the biosolution sample pH from its original pH to pH L is constant with each successive titration.

48. The process of claim 47, wherein a decreasing trend in the volume of acid required to reduce the biosolution sample to pH L with each successive titration is followed by increasing the addition of the alkali earth or alkali metals to the bioreactor.

49. The process of claim 47, wherein an increasing trend in the volume of acid required to reduce the biosolution sample to pH L with each successive titration is followed by decreasing the addition of the alkali earth or alkali metals to the bioreactor.

50. The process of claim 37, wherein the maintenance of concentrations in the biosolution comprises:
   a) obtaining a sample of the biosolution;
   b) allowing solids to settle in the sample, and obtaining a biolsolution sample free of sulfur solids;
   c) titrating an aliquot of a stock solution containing copper and dilute mineral acid with the biosolution sample free of sulfur solids, until the oxidation-reduction-potential (ORP) of the solution is reduced from the original ORP value to ORP L;
   d) recording the volume of biosolution consumed during the titration;
   e) repeating steps a) and d) at least once;
   f) adjusting the variable rate of providing hydrogen and/or carbon monoxide to the biosolution based on the volume of biosolution required to reduce the ORP of the stock solution from the original ORP to ORP L.

51. The process of claim 50, wherein a decreasing trend in the volume of biosolution consumed is followed by decreasing the rate of providing hydrogen and/or carbon monoxide to the biosolution.

52. The process of claim 50, wherein an increasing trend in the volume of biosolution consumed is followed by increasing the rate of providing hydrogen and/or carbon monoxide to the biosolution to increase the rate of $H_2S$ production.

53. The process of claim 50, wherein, in the titrating step:
   a) the copper concentration in the stock solution is from 0.01 to 10 g/L or about 6 g/L;
   b) the concentration of mineral acid in the stock solution is from 0.02 to 0.5 N, or about 0.2 N;
   c) the volume of the stock solution used during the titration is from 10 to 1000 mL, or about 100 mL;
   d) the ORP value L is from −150 mV to +250 mV, or from about −50 mV to about +150 mV; and,
   e) the ORP values are measured with respect to a Ag/AgCl reference.

54. The process of claim 1, wherein the pH of the biosolution is maintained at a pH greater than about pH 7.5 by coordinating one or more of:
   a) controlling the flow of gas that is allowed to enter the bioreactor; and
   b) addition of carbonate, bicarbonate, and/or hydroxide of alkali or alkali earth metalsto the bioreactor.

55. The process of claim 1, further comprising maintaining a constant pressure in the bioreactor vessel at a setpoint that is greater than atmospheric pressure.

56. The process of claim 55, wherein the constant pressure is maintained by the addition of an inert pressurizing gas to the bioreactor.

57. The process of claim 56, wherein addition of hydrogen and/or carbon monoxide to the bioreactor is discontinued when the pressure inside the bioreactor reaches a predetermined maximum value.

58. The process of claim 1, wherein a species of photoautotrophic algae that sequesters carbon from the atmosphere is treated to provide an algae liquor that is fed into the bioreactor as an electron donor, and as a carbon source.

59. The process of claim 1, wherein conditions in the bioreactor are adjusted to provide a maximum rate of $H_2S$ gas production.

60. A process for producing $H_2S$ comprising:
   a) continuously providing an electron donor at a variable rate to a biosolution comprising sulphur-reducing bacteria;
   b) reacting elemental sulphur with $HS^{31}$ in the biosolution to form soluble polysulphide;
   c) providing said polysulphide to a bioreactor having the biosolution, thereby producing $H_2S$ gas in the bioreactor; and
   d) continuously removing $H_2S$ gas from the bioreactor;
   wherein biosolution chemistry is maintained so that the concentration of bisulphide and polysulphide species dissolved in the biosolution is at a substantially constant concentration that supports a selected rate of elemental sulfur dissolution, so that an average rate of providing polysulphide to the sulphur-reducing bacteria is equal to an average rate of polysulphide consumption by the sulphur-reducing bacteria; and, wherein the step of maintaining biosolution chemistry comprises:
   adjusting the flow rate of $H_2S$ gas that is removed from the bioreactor to maintain the pH in the bioreactor at a pH greater than about pH 6.8, or greater than about 7.5; and,
   maintaining the conductivity of the biosolution at between about 6 mS/cm and about 25 mS/cm by the addition of carbonate, bicarbonate, or hydroxide of alkali or alkali earth metals to the bioreactor.

61. A process for producing $H_2S$ gas from a culture of sulphur-reducing bacteria in a biosolution in a bioreactor, the process comprising:
   feeding elemental sulfur and an electron donor to the culture at a selected sulfur-to-electron donor ratio;
   reacting elemental sulfur with HS− to form water soluble polysulphides;
   maintaining biosolution chemistry so that a sufficient inventory of suspended solid sulfur and dissolved polysulphides is provided in the bioreactor to support the selected rate of $H_2S$ production, and so that the concentration of bisulphide and polysulphide species dissolved in the biosolution is at a substantially constant concentration that supports a selected rate of elemental sulfur dissolution;
   removing $H_2S$ gas from the bioreactor;
   wherein an average rate of providing polysulphide to sulphur-reducing bacteria is equal to an average rate of polysulphide consumption by the sulphur-reducing bacteria; and wherein the step of maintaining biosolution chemistry comprises:
   adjusting the flow rate of $H_2S$ gas that is removed from the bioreactor to maintain the pH in the bioreactor at a pH greater than about pH 6.8, or greater than about 7.5; and,
   maintaining the conductivity of the biosolution at between about 6 mS/cm and about 25 mS/cm by the addition of carbonate, bicarbonate, or hydroxide of alkali or alkali earth metals to the bioreactor.

62. A process for producing $H_2S$ comprising:
   a) continuously providing an electron donor at a variable rate to a biosolution comprising sulphur-reducing bacteria;
   b) maintaining the respective concentrations of bisulphide, polysulphide, electron donor and bicarbonate species dissolved in the biosolution at levels that support a selected rate of elemental sulfur dissolution, so that polysulphide formed during the sulfur dissolution process is provided to the microbial culture at a substantially constant concentration and at an average rate that is equal to the average rate of polysulphide consumption by the culture; and, c) continuously removing $H_2S$ gas from the bioreactor, wherein the rate of removing $H_2S$ from the bioreactor is equal to the rate of $H_2S$ production; and, wherein the step of maintaining biosolution chemistry comprises:
adjusting the flow rate of $H_2S$ gas that is removed from the bioreactor to maintain the pH in the bioreactor at a pH greater than about pH 6.8, or greater than about 7.5; and,
maintaining the conductivity of the biosolution at between about 6 mS/cm and about 25 mS/cm by the addition of carbonate, bicarbonate, or hydroxide of alkali or alkali earth metals to the bioreactor.

63. A process for producing $H_2S$ comprising:
a) continuously providing an electron donor at a variable rate to a biosolution comprising sulphur-reducing bacteria;
b) reacting elemental sulphur with $HS^-$ to form soluble polysulphide;
c) maintaining biosolution chemistry so that said polysulphide inventory in the bioreactor at a level necessary to yield the required rate of $H_2S$ production wherein the step of maintaining biosolution chemistry comprises:
adjusting the flow rate of $H_2S$ gas that is removed from the bioreactor to maintain the pH in the bioreactor at a pH greater than about pH 6.8, or greater than about 7.5; and,
maintaining the conductivity of the biosolution at between about 6 mS/cm and about 25 mS/cm by the addition of carbonate, bicarbonate, or hydroxide of alkali or alkali earth metals to the bioreactor;
d) maintaining substantially constant concentrations of bisulphide, and bicarbonate in the bioreactor to support the required rate of $H_2S$ production; and
e) continuously removing $H_2S$ gas from the bioreactor;
wherein an average rate of providing polysulphide to sulphur-reducing bacteria is equal to an average rate of polysulphide consumption by the sulphur-reducing bacteria.

* * * * *